(12) United States Patent
Izumida et al.

(10) Patent No.: US 9,776,029 B2
(45) Date of Patent: Oct. 3, 2017

(54) FIRE EXTINGUISHING AGENT AND FIRE EXTINGUISHING METHOD USING SAME

(75) Inventors: Masashi Izumida, Takasago (JP);
Satohiro Yanagisawa, Minato-ku (JP);
Yasuyoshi Ueda, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 387 days.

(21) Appl. No.: 14/234,303

(22) PCT Filed: Jul. 23, 2012

(86) PCT No.: PCT/JP2012/068584
§ 371 (c)(1),
(2), (4) Date: May 1, 2014

(87) PCT Pub. No.: WO2013/015241
PCT Pub. Date: Jan. 31, 2013

(65) Prior Publication Data
US 2014/0290970 A1    Oct. 2, 2014

(30) Foreign Application Priority Data

Jul. 22, 2011 (JP) ................................ 2011-160524

(51) Int. Cl.
*A62D 1/00* (2006.01)
*C07K 14/785* (2006.01)
*A62D 1/02* (2006.01)

(52) U.S. Cl.
CPC .............. *A62D 1/0042* (2013.01); *A62D 1/00* (2013.01); *A62D 1/0014* (2013.01); *A62D 1/0071* (2013.01); *C07K 14/785* (2013.01)

(58) Field of Classification Search
CPC ...... A62D 1/0042; A62D 1/00; A62D 1/0014; A62D 1/0071; C07K 14/785
See application file for complete search history.

(56) References Cited

U.S. PATENT DOCUMENTS 5,756,471 A * 5/1998 Hillion .................. A61K 8/062
                                                    514/25
6,183,736 B1 * 2/2001 Moyne ................... A01N 37/46
                                                    424/405
(Continued)

FOREIGN PATENT DOCUMENTS

CN         101564582 A      10/2009
DE    10 2007 063 429 A1    6/2009
(Continued)

OTHER PUBLICATIONS

Extended European Search Report issued Feb. 25, 2015 in Patent Application No. 12818268.0.
(Continued)

*Primary Examiner* — Peter F Godenschwager
*Assistant Examiner* — Andrew J Oyer
(74) *Attorney, Agent, or Firm* — Oblon, McClelland, Maier & Neustadt, L.L.P.

(57) ABSTRACT

The objective of the present invention is to provide an extinguishing agent which has excellent fire-extinguishing property and which exhibits high safety to the environment and human body. The fire extinguishing agent of the present invention is characterized in comprising a biosurfactant.

21 Claims, 1 Drawing Sheet

(56) References Cited

U.S. PATENT DOCUMENTS

| | | | |
|---|---|---|---|
| 7,887,906 B2 * | 2/2011 | Ohkubo | H01B 1/127 252/500 |
| 2003/0018306 A1 | 1/2003 | Bucay-Couto et al. | |
| 2003/0229065 A1 | 12/2003 | Levy et al. | |
| 2004/0106553 A1 | 6/2004 | Alekshun et al. | |
| 2004/0171512 A1 | 9/2004 | Furuta et al. | |
| 2004/0219125 A1 * | 11/2004 | Yoneda | A61K 8/042 424/70.21 |
| 2005/0124678 A1 | 6/2005 | Levy et al. | |
| 2005/0266036 A1 * | 12/2005 | Awada | A01N 63/02 424/405 |
| 2005/0271698 A1 | 12/2005 | Bucay-Couto et al. | |
| 2005/0281820 A1 * | 12/2005 | Hicks | A61K 9/0014 424/145.1 |
| 2008/0311234 A1 | 12/2008 | Yoneda et al. | |
| 2009/0126948 A1 * | 5/2009 | DeSanto | A62C 3/02 169/45 |
| 2009/0131401 A1 | 5/2009 | Levy et al. | |
| 2010/0227850 A1 | 9/2010 | Alekshun et al. | |
| 2011/0230523 A1 | 9/2011 | Levy et al. | |

FOREIGN PATENT DOCUMENTS

| | | |
|---|---|---|
| JP | 50-142483 | 11/1975 |
| JP | 61-197659 | 9/1986 |
| JP | 3-154627 | 7/1991 |
| JP | 2003-13093 | 1/2003 |
| JP | 2004-27133 | 1/2004 |
| JP | 2005-306863 | 11/2005 |
| JP | 2009-291257 | 12/2009 |
| RU | 2014858 C1 | 6/1994 |
| WO | 2009/148039 A1 | 12/2009 |

OTHER PUBLICATIONS

International Search Report issued Oct. 23, 2012, in PCT/JP2012/068584, filed Jul. 23, 2012.

Choi et al., "R&D of Biosurfactants as New Materials" Oleo Science, vol. 2, No. 10, 2002, pp. 649-657 (with partial English translation).

Assessment report: Caspofungin Accord; from European Medicines Agency, Dec. 17, 2015, 18 pages.

* cited by examiner

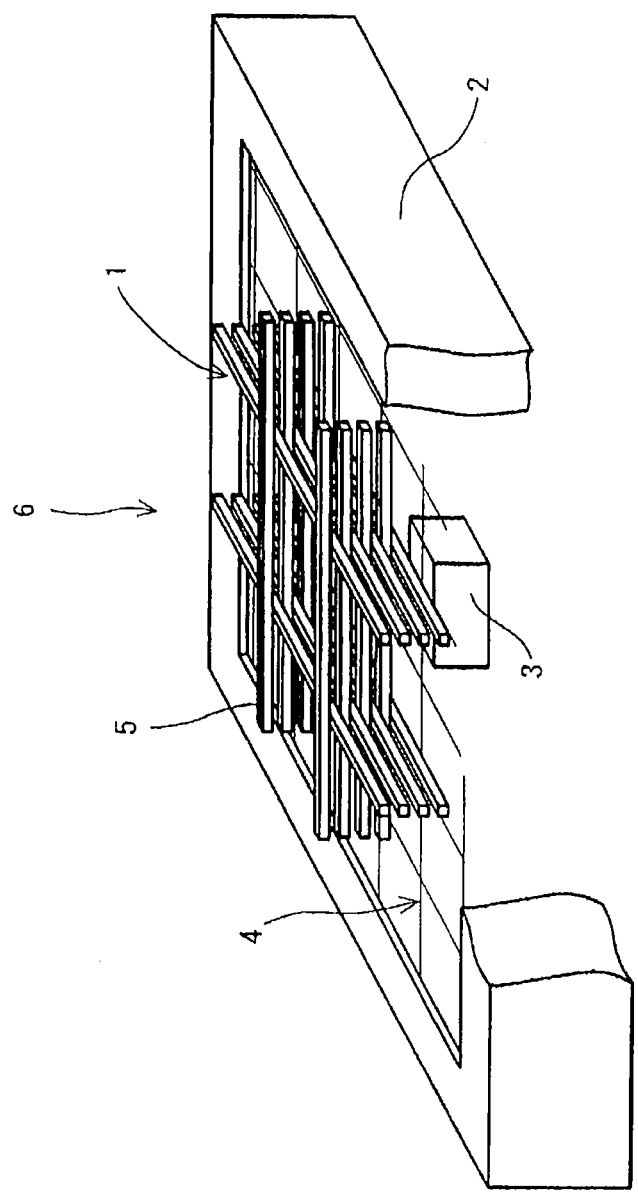

FIRE EXTINGUISHING AGENT AND FIRE EXTINGUISHING METHOD USING SAME

TECHNICAL FIELD

The present invention relates to a fire extinguishing agent which contains a biosurfactant, and a method for extinguishing a fire in which the fire extinguishing agent is used.

BACKGROUND ART

Even in Japan only, tens of thousands of fires occurs every year. Therefore, a fire is a serious problem for the global environment and human society. When a fire breaks out, it is important to efficiently extinguish the fire in order to minimize damage. As a conventional extinguishing agent, water and an aqueous extinguishing agent have been used. As a general aqueous extinguishing agent, APC extinguishing agent mainly consisting of potassium carbonate aqueous solution is known. Such APC extinguishing agent contains a synthetic surfactant in order to lower the surface tension thereof and improve wetting property and permitting property to a combustible material such as woods, fiber and resin. In addition, adhesive property is improved, since APC extinguishing agent is foamed by a synthetic surfactant. Due to the above properties, fire extinguishing effect, reheat-prevention effect and fire spread-prevention effect are improved, and it is known that APC extinguishing agent can extinguish a fire in a shorter time and in a smaller amount than water alone.

However, even for the above-described fire-extinguishing performance, low safety of a conventional extinguish agent for the environment and human body is acknowledged as a problem.

For example, though APC extinguishing agent is particularly effective in extinguishing a fire caused due to cooking oil having high temperature, the agent shows strong basicity and the pH thereof is 12 to 13. Therefore, furniture, eating utensils, a device and the like to which the agent adheres should be thoroughly washed or discarded. In addition, a metallic structural body, metallic fittings or the like do not burn but may possibly become eroded by APC extinguishing agent. Furthermore, when a conventional extinguishing agent which contains a synthetic surfactant is sprayed, a secondary damage after fire extinguishment is caused. For example, such an extinguishing agent is highly toxic to an aquatic organism.

Under the above-described circumstances, an extinguishing agent which contains a natural surfactant, such as lecithin, saponin and casein, was recently developed in order to reduce pressure on the environment or human body (Patent Document 1).

PRIOR ART

Patent Document

Patent Document 1: JP 2009-291257 A

DISCLOSURE OF THE INVENTION

Problems to be Solved by the Invention

An extinguishing agent which contains a natural surfactant is representatively described in Patent Document 1. The extinguishing agent is safe for human body and the environment; on the other hand, the fire-extinguishing performance thereof is unsatisfactory. Therefore, the usefulness of the extinguishing agent is limited.

Means for Solving the Problems

The inventors of the present invention intensively studied for solving the above problem. As a result, the inventors completed the present invention by finding that a biosurfactant among a natural surfactant is especially safe for the environment and human body, and can remarkably improve fire-extinguishing performance of an extinguishing agent.

The present invention relates to a fire extinguishing agent which is characterized in comprising a biosurfactant. In addition, the present invention relates to a fire extinguishing method which is characterized in comprising the step of using the fire extinguishing agent. Furthermore, the present invention relates to a fire extinguisher which is characterized in comprising the fire extinguishing agent and a fire extinguishing system.

Effect of the Invention

The fire extinguishing agent of the present invention exhibits a superior fire-extinguishing efficiency in comparison with other extinguishing agent which contains a natural surfactant. As more preferred property, a concentration and an amount to be used of the fire extinguishing agent according to the present invention can be substantially reduced due to an excellent extinguishing performance in comparison with a conventional extinguishing agent containing a synthetic surfactant. In other words, the extinguishing agent of the present invention has excellent properties due to only a small amount to be contained of a biosurfactant having high safety. For example, the extinguishing agent of the present invention has low load on the environment and human body. Therefore, the extinguishing agent of the present invention can be expected to exhibit superior effect on not only a fire of a building but also a big forest fire.

BRIEF DESCRIPTION OF THE DRAWING

FIG. 1 is a schematic perspective view which partly has notch and which demonstrates a device used for fire-extinguishing performance test of the extinguishing agents of Examples 1 to 10 according to the present invention and Comparative examples 1 to 8.

MODE FOR CARRYING OUT THE INVENTION

Hereinafter, the present invention is described in detail.

The extinguishing agent of the present invention is characterized in comprising a biosurfactant.

A biosurfactant is a natural compound which is produced by a microorganism, and has a very high safety to the environment and human body since a biosurfactant exhibits a high biodegradability and low skin irritation. Such a biosurfactant is exemplified by a glycolipid biosurfactant such as mannosylerythritol lipid, sophorolipid, trehalose lipid and rhamnolipid; a fatty acid biosurfactant such as spiculisporic acid; a polymer biosurfactant such as emulsan; a lipopeptide compound biosurfactant such as arthrofactin and surfactin; and a salt thereof. The biosurfactant is not limited to the above examples.

Among the above-described examples, sophorolipid or a salt thereof is preferred as a glycolipid biosurfactant, spiculisporic acid is preferred as a fatty acid biosurfactant, and surfactin is preferred as a lipopeptide compound biosurfactant. A particularly preferred biosurfactant is a lipopeptide compound biosurfactant or a salt thereof, and specifically a lipopeptide compound biosurfactant or a salt thereof which is produced by a bacterium of genus bacillus, such as *Bacillus subtilis*. In addition, surfactin or a salt thereof is exemplified as a preferred example.

Surfactin or a salt thereof is represented by the following formula (1):

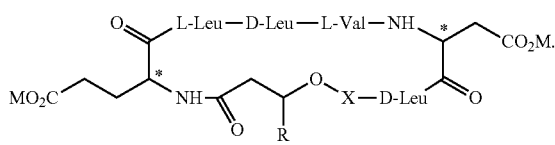

Hereinafter, the above surfactin or a salt thereof is referred to as "compound (1)".

In the formula (1), the symbol "*" indicates an optically-active center.

X is any one of amino acids selected from leucine, isoleucine or valine.

R is a linear or branched alkyl group having a carbon number of not less than 1 and not more than 20.

In the present invention, an alkyl group having a carbon number of not less than 1 and not more than 20 is exemplified by a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, a nonadecyl group and an icosanyl group.

A branched alkyl group having a carbon number of not less than 1 and not more than 20 is exemplified by an isopropyl group, an isobutyl group, a sec-butyl group, a tert-butyl group, an isopentyl group, a neopentyl group, a tert-pentyl group, an isohexyl group, a 7-methyloctyl group, a 8-methylnonyl group, a 9-methyldecyl group, a 10-methylundecyl group, a 11-methyldodecyl group, a 12-methyltridecyl group, a 13-methyltetradecyl group, a 14-methylpentadecyl group, a 15-methylhexadecyl group, a 16-methylheptadecyl group, a 17-methyloctadecyl group, a 18-methylnonadecyl group, a 6-methyloctyl group, a 7-methylnonyl group, a 8-methyldecyl group, a 9-methylundecyl group and a 10-methyldodecyl group.

The above-described alkyl group may be substituted with one or not less than two substituents. Such a substituent is exemplified by an amino group, a hydroxy group, a phenyl group, an aryl group, an alkanoyl group, an alkenyl group, an alkynyl group, an alkoxy group, a nitro group and a halogen atom.

M is a hydrogen atom or may form a salt with surfactin. It is preferred that M forms a salt with surfactin. A preferred M is not limited as long as the M can form such a salt, and is particularly preferably an alkali metal, an alkaline earth metal or an ammonium.

In the present invention, an alkali metal is not particularly limited, and exemplified by lithium, sodium and potassium. Among the examples, sodium is preferred.

An alkaline earth metal is not particularly limited, and exemplified by beryllium, magnesium and calcium.

An ammonium is not particularly limited as long as the ammonium can form a salt with surfactin, and may be substituted. Such an ammonium is exemplified by an unsubstituted ammonium, a monosubstituted ammonium, a disubstituted ammonium, a trisubstituted ammonium and tetrasubstituted ammonium.

A substituent of the ammonium is exemplified by an organic group. Such an organic group is exemplified by an alkyl group such as a methyl group, an ethyl group, a n-propyl group, an isopropyl group, a n-butyl group and a tert-butyl group; an aralkyl group such as a benzyl group, a methylbenzyl group and a phenylethyl group; and an aryl group such as a phenyl group, a toluyl group and a xylyl group.

The ammonium is more specifically exemplified by methylammonium, ethylammonium, benzylammonium, anilinium, diethylammonium, dicyclohexylammonium, pyrrolidinium, morpholinium, N-benzyl-N-ethylammonium, N-ethylanilinium, triethylammonium, tetramethylammonium, tetraethylammonium and pyridinium. The above organic group may be further substituted with one or not less than two substituents.

One kind of the above biosurfactant or not less than two kinds of the above biosurfactant may be used. It is preferred that surfactin or a salt thereof is used alone or combined with other biosurfactant, such as a glycolipid biosurfactant, a fatty acid biosurfactant, a polymer biosurfactant, and a lipopeptide compound biosurfactant other than surfactin. The extinguishing agent which contains surfactin or a salt thereof has superior stability of foam. A combination of two or more biosurfactants is exemplified by surfactin or a salt thereof and a glycolipid biosurfactant such as mannosylerythritol lipid and sophorolipid, surfactin or a salt thereof and a fatty acid biosurfactant such as spiculisporic acid, surfactin or a salt thereof and a polymer biosurfactant such as emulsan, surfactin or a salt thereof and a lipopeptide compound biosurfactant such as arthrofactin. The combination is not limited to the above examples.

The biosurfactant to be used is not limited to one obtained by microbial fermentation and may be obtained by chemical synthesis.

A formulation of the extinguishing agent containing a biosurfactant is not particularly limited, and exemplified by powder, solution, foam and paste. The preferred formulation to be used is an aqueous solution or a foamed solution.

An amount of the biosurfactant to be used in the extinguishing agent of the present invention is not particularly limited. With respect to a ratio by weight of the biosurfactant to be used in the aqueous solution-type extinguishing agent, the lower limit is not less than 0.00001 wt %, preferably not less than 0.0001 wt %, even more preferably not less than 0.001 wt %, even more preferably not less than 0.01 wt %, and most preferably not less than 0.1 wt %. The upper limit thereof is, for example, not more than 50 wt %. preferably not more than 10 wt %, and even more preferably not more than 1 wt %.

With respect to a solution of the extinguishing agent, a solution in which concentrations of each component are properly adjusted as described above may be preliminarily prepared and conveyed to the site of a fire to be extinguished. Alternatively, a high concentration solution may be conveyed to the site of a fire and diluted. However, an embodiment is not particularly limited to the above examples.

Into the extinguishing agent, an additive agent which is used in a general extinguishing agent other than a biosurfactant can be added with no specific restriction. In the present invention, as the extinguishing agent, an aqueous extinguishing agent of which main component is water, APC extinguishing agent of which main component is an alkali salt such as potassium carbonate, a neutral extinguisher which contains a phosphate salt, potassium salt and the like, a protein foam fire extinguishing agent are exemplified. However, the extinguishing agent is not limited to the above examples.

Other component used in the extinguishing agent is exemplified by a polyol such as glycerin; a higher fatty acid and a derivative thereof, such as palmitic acid and myristic acid; a higher alcohol and a derivative thereof, such as lauryl alcohol and cetyl alcohol; an organic acid and a derivative thereof, such as citric acid, tartaric acid and lactic acid; a non-ionic surfactant such as a polyoxyethylene alkyl ether and a polyhydric alcohol fatty acid ester; an anion surfactant such as an alkyl sulfate ester salt, a polyoxyethylene alkyl ether phosphate and a dodecylbenzene sulfonate; a cation surfactant such as an alkyltrimethylammonium salt; an ampholytic betaine-type surfactant such as an alkyldimethylbetaine; a water-soluble polymer such as methylcellulose, polyvinyl alcohol and sodium alginate; a pH adjuster such as succinic acid, gluconic acid, a carbonate and a hydrogen-carbonate; a chelating agent such as L-glutamic acid diacetate, citrate, tartrate, oxalate, malate, gluconate and phytate; a thickener such as pectin and xanthane gum; an antifreeze agent such as ethylene glycol and an antifreeze protein; a base such as an alkali salt and ammonia; a mineral acid such as hydrochloric acid, sulfuric acid and nitric acid; a lower alcohol such as methanol and ethanol; water. However, an additive agent is not limited to the above examples.

A biosurfactant which is one of the components of the extinguishing agent is used as not only a main component for fire extinction but also an auxiliary agent for fire extinction.

A fire extinguishing performance of the above-described extinguishing agent characterized in comprising a biosurfactant is improved in comparison with a conventional extinguishing agent and water.

For example, fire extinguishing performance can be evaluated as a fire-extinguishing speed, which is calculated from a time required for extinguishing a fire, and a fire-extinguishing efficiency, i.e. a degree of reduction of an extinguishing agent, which is calculated from an amount of an extinguishing agent to extinguish a fire.

In particular, it is most important to improve a fire-extinguishing speed, since the speed is closely related to the safety of a sufferer and a firefighter involved in a rescue operation, and further related to the prevention of the expansion of damage, such as spread of a fire. In addition, for example, if a fire-extinguishing efficiency is improved, it becomes possible to extinguish a fire by smaller equipment and improve efficiency in carrying required equipment to a fire. Furthermore, the number of firefighter required at a fire can be decreased, and the load on firefighter who wears equipment for a task can be reduced. Therefore, efficiency of fire-fighting operation itself can be dramatically improved. As described above, improvement of a fire-extinguishing speed and a fire-extinguishing efficiency can greatly contribute to lifesaving and minimization of damage.

A method for using the extinguishing agent of the present invention characterized in comprising a biosurfactant is not particularly limited, and exemplified by a method in which the extinguishing agent is filled in a fire extinguisher and sprayed, a method in which the extinguishing agent is sprayed by a pressure-feed using a pump from a storage container or a tank, a method in which the extinguishing agent is sprayed using a sprayer, a method in which the extinguishing agent is sprayed from the sky using a helicopter or a plane, and a method in which the extinguishing agent is filled in a heat-melt resin container or a heat-breakable container to be a fire-extinguishing grenade and the obtained fire-extinguishing grenade is directly thrown in a fire. When the extinguishing agent is sprayed using a fire extinguisher or by a pressure-feed using a pump, the tip nozzle may be replaced with a bubble generating nozzle and the extinguishing agent may be foamed to be used. In such a case, the extinguishing agent is foamed and a fire can be extinguished more efficiently. A biosurfactant used in the present invention is especially effective due to the foaming stability thereof. A method for foaming the extinguishing agent is not particularly limited, and exemplified by a method in which a nozzle to take in air and generate foam is used when the extinguishing agent is sprayed and a method in which the extinguishing agent is preliminarily foamed in a mixer.

In the range of the present invention, each fire extinguishing system for carrying out the above-described method for using the extinguishing agent is included. Such a fire extinguishing system is exemplified by Fire extinguishing system 1 which includes a fire extinguisher containing the extinguishing agent and a spreading means or a spraying means attached to the fire extinguisher, Fire extinguishing system 2 which includes a container containing the extinguishing agent and a spreading means or a spraying means attached to the container and a pressurizing means for feeding the extinguishing agent by pressure from the container to the spraying means, and a plane or a helicopter fitted with the above Fire extinguishing system 1 or 2. The above-described spreading means and spraying means are exemplified by a spraying nozzle and a bubble generating nozzle.

The extinguishing agent comprising a biosurfactant has an effect on A-type fire, i.e. an ordinary fire, and a fire due to cooking oil. In addition, since the extinguishing agent can be foamed and cover over a subject to be extinguished, the extinguishing agent has an effect of preventing a flammable gas from evaporating and spreading in B-type fire, i.e. an oil fire. Therefore, the present invention has an effect on any one of A-type fire, i.e. an ordinary fire, B-type fire, i.e. an oil fire, and a fire due to cooking oil. Furthermore, the present invention can be applied to C-type fire, i.e. a fire due to electricity, since the same extinguishing component can be used for C-type fire though the spraying method is different from that for other fires.

The present application claims the benefit of the priority date of Japanese patent application No. 2011-160524 filed on Jul. 22, 2011, and all of the contents of the Japanese patent application No. 2011-160524 filed on Jul. 22, 2011 are incorporated by reference.

EXAMPLES

Hereinafter, specific Examples of the present invention are described. However, the present invention is not intended to be limited by the Examples.

Examples 1 to 10

Fire-extinguishing Performance Test

Biosurfactant aqueous solutions (200 g) which contained sodium surfactin, i.e. "SF", and sodium sophorolipid, i.e. SL, singly or in combination in a concentration described in Table 1 were prepared as extinguishing agents. In addition, a combustion test apparatus (6) was prepared as demonstrated in FIG. 1 using 16 pieces of wood (5) having a size of 2 mm×2 mm×50 mm and 6 g of a solid fuel (3) containing methanol as a main component. The above pieces of wood (5) were piled up in 8 layers by 2 pieces. In each layer, 2 pieces were placed parallel to each other. The 2 pieces of wood (5) in each layer were placed in a direction perpendicular to the pieces of wood (5) in the next upper or lower layer. The piled wood (5) is referred to as "orderly and squarely piled up scantling woods (1)". The above apparatus was equipped with a metal platform (2) and a mesh (4) having 10 cm squares was placed on the superior surface of the platform (2). The above-described orderly and squarely piled up scantling woods (1) was placed in the center of the mesh (4). The above-described solid fuel (3) was placed about 3 cm under the orderly and squarely piled up scantling woods (1). The orderly and squarely piled up scantling woods (1) was fired by igniting the solid fuel (3). After 1 minute from the ignition, the solid fuel (3) was removed. Then, the above-described extinguishing agent was sprayed about 30 cm away from the orderly and squarely piled up scantling woods (1). The fire extinguishing completion was defined as until smoke disappeared, and it was confirmed that reheat and smoking were not observed in the next 2 minutes. The time to the fire extinguishing completion was evaluated as a time required for extinguishing a fire, and an amount of the extinguishing agent sprayed until the fire was extinguished was evaluated as a use amount of the extinguishing agent.

Permeability Performance Test

A paper towel having a size of 38 cm×33 cm ("Kimtowel (registered trademark)" manufactured by NIPPON PAPER CRECIA Co., LTD.) was cut into a size of 2 cm×2 cm, and the center thereof was secured with a staple to be a test piece. A biosurfactant aqueous solution (100 mL) having concentration described in Table 1 was added in a beaker having the same volume. The above test piece was slowly placed on the surface of the solution. The time from when the test piece was placed till when the test piece sank to the bottom was measured, and the measured time was used for evaluating the permeability performance.

Foam Stability Performance Test

Into a 100 mL measuring cylinder, 20 mL of a biosurfactant aqueous solution having a concentration described in Table 1 was added. The measuring cylinder was sealed with a sealing material film made of paraffin ("parafilm (registered trademark)" manufactured by Nikkei Products Co., Ltd.), and then the solution was vigorously stirred for 30 seconds. A volume of foam was measured immediately after stirring and 5 minutes after stirring. A ratio of foam volume 5 minutes after stirring relative to foam volume immediately after stirring is demonstrated in Table 1.

Comparative Examples 1 to 8

Tests similarly to the above-described Examples were carried out except that sodium caseinate, soybean lecithin or soybean saponin as a natural surfactant or sodium lauryl sulfate as a synthetic surfactant was used instead of a biosurfactant. In addition, similar tests were carried out using water as control.

An extinguishing speed was evaluated as a value which was obtained by dividing an extinguishing time measured in each example by extinguishing time measured using distilled water as an extinguishing agent. An extinguishing efficiency was evaluated as a value which was obtained by dividing an amount of an extinguishing agent measured in each example by an amount of distilled water used as an extinguishing agent.

TABLE 1

| | | Extinguishing time | | Amount of extinguishing agent to be used | | Function | |
|---|---|---|---|---|---|---|---|
| | Extinguishing agent | Extinguishing time (sec) | Extinguishing speed vs water (times) | Use amount (g) | Extinguishing efficiency vs water (times) | Permeability (sec) | Foam stability (%) |
| Comparative example 1 | distilled water | 180 | 1.0 | 165 | 1.0 | 720 | 0 |
| Example 1 | 3% surfactin Na (SF) aqueous solution | 59 | 3.1 | 53 | 3.1 | 5 | 91 |
| Example 2 | 1% surfactin Na (SF) aqueous solution | 58 | 3.1 | 54 | 3.1 | 5 | 90 |
| Example 3 | 0.1% surfactin Na (SF) aqueous solution | 65 | 2.8 | 55 | 3.0 | 5 | 92 |
| Example 4 | 0.01% surfactin Na (SF) aqueous solution | 96 | 1.9 | 84 | 2.0 | 6 | 90 |
| Example 5 | 1% sophorolipid Na (SL) aqueous solution | 85 | 2.1 | 60 | 2.8 | 7 | 8 |
| Example 6 | 0.1% sophorolipid Na (SL) aqueous solution | 90 | 2.0 | 65 | 2.5 | 7 | 5 |
| Example 7 | 0.01% sophorolipid Na (SL) aqueous solution | 119 | 1.5 | 90 | 1.8 | 11 | 5 |
| Example 8 | 1% mixed aqueous solution (SF:SL = 1:1) | 60 | 3.0 | 57 | 2.9 | 4 | 100 |
| Example 9 | 0.1% mixed aqueous solution (SF:SL = 1:1) | 90 | 2.0 | 77 | 2.1 | 5 | 90 |
| Example 10 | 0.01% mixed aqueous solution (SF:SL = 1:1) | 90 | 2.0 | 78 | 2.1 | 4 | 90 |
| Comparative example 2 | 1% casein Na aqueous solution | 94 | 1.9 | 91 | 1.8 | 220 | 60 |
| Comparative example 3 | 0.1% casein Na aqueous solution | 155 | 1.2 | 158 | 1.0 | 657 | 17 |
| Comparative example 4 | 0.01% soybean lecithin Na aqueous solution | 182 | 1.0 | 170 | 1.0 | 740 | 0 |
| Comparative example 5 | 0.1% soybean saponin Na aqueous solution | 154 | 1.2 | 144 | 1.1 | 700 | 5 |
| Comparative example 6 | 1% lauryl sulfate Na aqueous solution | 59 | 3.1 | 55 | 3.0 | 5 | 88 |

TABLE 1-continued

|  | Extinguishing agent | Extinguishing time | | Amount of extinguishing agent to be used | | Function | |
|---|---|---|---|---|---|---|---|
|  |  | Extinguishing time (sec) | Extinguishing speed vs water (times) | Use amount (g) | Extinguishing efficiency vs water (times) | Permeability (sec) | Foam stability (%) |
| Comparative example 7 | 0.1% lauryl sulfate Na aqueous solution | 67 | 2.7 | 58 | 2.8 | 5 | 85 |
| Comparative example 8 | 0.01% lauryl sulfate Na aqueous solution | 150 | 1.2 | 145 | 1.1 | 720 | 10 |

It was clarified from the above Table that when a biosurfactant aqueous solution is used as an extinguishing agent, permeability is improved as well as fire-extinguishing speed and f ire-extinguishing efficiency are preferably improved. In particular, it was demonstrated that when a biosurfactant aqueous solution is used, fire-extinguishing speed and fire-extinguishing efficiency are remarkably improved since not only permeability but also foam stability is improved. With respect to the effects when a biosurfactant aqueous solution was used, both of fire-extinguishing speed and fire-extinguishing efficiency were preferably increased about twofold in comparison with the case of natural surfactants and about threefold in comparison with the case of water. In addition, the effect was equal or higher than that of a synthetic surfactant, which generally has high-performance, in some cases. It was clarified from the above results that the extinguishing agent containing a biosurfactant has excellent properties and safety for the environment and human body.

The invention claimed is:

1. A method for extinguishing a fire, comprising:
applying a fire extinguishing agent to a fire,
wherein the fire extinguishing agent comprises a lipopeptide compound or a salt thereof.

2. The method according to claim 1, wherein the fire extinguishing agent further comprises at least one component selected from the group consisting of a glycolipid biosurfactant or its salt; a fatty acid biosurfactant or its salt; and a polymer biosurfactant or its salt.

3. The method according to claim 1, wherein the fire extinguishing agent is applied in a form of powder, solution, foam or paste.

4. The method according to claim 1, wherein the fire extinguishing agent is applied in a form of a foamed solution.

5. The method according to claim 1, wherein the fire extinguishing agent is applied in a form of an aqueous solution.

6. The method according to claim 5, wherein the fire extinguishing agent comprises 0.001 wt % or more and 50 wt % or less of the lipopeptide compound or a salt thereof.

7. The method according to claim 5, wherein the fire extinguishing agent comprises 0.01 wt % or more and 10 wt % or less of the lipopeptide compound or a salt thereof.

8. The method according to claim 5, wherein the fire extinguishing agent comprises 0.1 wt % or more and 1 wt % or less of the lipopeptide compound or a salt thereof.

9. The method according to claim 8, wherein the lipopeptide compound or a salt thereof comprises a surfactin or a salt thereof, and the fire extinguishing agent further comprises a glycolipid biosurfactant or a salt thereof.

10. The method according to claim 8, wherein the lipopeptide compound or a salt thereof is sodium surfactin.

11. The method according to claim 10, wherein the fire extinguishing agent further comprises sodium sophorolipid.

12. The method according to claim 1, wherein the fire extinguishing agent further comprises at least one compound selected from the group consisting of glycerin, palmitic acid, myristic acid, lauryl alcohol, cetyl alcohol, citric acid, tartaric acid, lactic acid, a polyoxyethylene alkyl ether, a polyhydric alcohol fatty acid ester, an alkyl sulfate ester salt, a polyoxyethylene alkyl ether phosphate, a dodecylbenzene sulfonate, an alkyltrimethylammonium salt, an alkyldimethylbetaine, methylcellulose, polyvinyl alcohol, sodium alginate, succinic acid, gluconic acid, a carbonate, a hydrogencarbonate, L-glutamic acid diacetate, citrate, tartrate, oxalate, malate, gluconate or phytate, pectin, xanthane gum, ethylene glycol, an antifreeze protein, an alkali salt, ammonia, hydrochloric acid, sulfuric acid, nitric acid, methanol, ethanol, and water.

13. The method according to claim 1, wherein the lipopeptide compound or a salt thereof is produced by a bacterium of genus *bacillus*.

14. The method according to claim 1, wherein the lipopeptide or a salt thereof is produced by *Bacillus subtilis*.

15. The method according to claim 1, wherein the lipopeptide compound or a salt thereof comprises a surfactin or a salt thereof, and the fire extinguishing agent further comprises a glycolipid biosurfactant or a salt thereof.

16. The method according to claim 1, wherein the lipopeptide compound or a salt thereof is sodium surfactin, and the fire extinguishing agent further comprises sodium sophorolipid.

17. The method according to claim 1, wherein the lipopeptide compound or a salt thereof comprises a surfactin or a salt thereof represented by the formula (1):

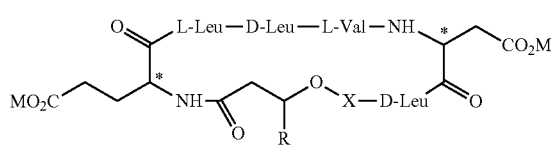

wherein
 * indicates an optically-active center;
 X is an amino acid selected from the group consisting of leucine, isoleucine and valine;
 R is a linear or branched alkyl group having 1 or more and 20 or less carbon atoms; and M is a hydrogen atom, an alkali metal, an alkaline earth metal or an optionally-substituted ammonium.

18. The method according to claim 17, wherein M is lithium, sodium or potassium.

19. The method according to claim 17, wherein M is sodium.

20. The method according to claim 17, wherein M is beryllium, magnesium or calcium.

21. A method for extinguishing a fire, comprising:
applying a fire extinguishing agent to a building fire or a forest fire,
wherein the fire extinguishing agent comprises a lipopeptide compound or a salt thereof.

* * * * *